(12) United States Patent
Leone, Jr.

(10) Patent No.: US 6,623,488 B1
(45) Date of Patent: *Sep. 23, 2003

(54) PELVIC ALIGNMENT ASSEMBLY

(75) Inventor: William Leone, Jr., Lighthouse Point, FL (US)

(73) Assignee: Leone Innovations Corporation, Lighthouse Point, FL (US)

( * ) Notice: Subject to any disclaimer, the term of this patent is extended or adjusted under 35 U.S.C. 154(b) by 62 days.

This patent is subject to a terminal disclaimer.

(21) Appl. No.: 09/976,413

(22) Filed: Oct. 12, 2001

Related U.S. Application Data

(63) Continuation-in-part of application No. 09/526,896, filed on Mar. 16, 2000, now Pat. No. 6,302,890.

(51) Int. Cl.$^7$ ............................................. A61B 17/58
(52) U.S. Cl. ............................................. 606/102; 606/91
(58) Field of Search ............................. 606/91, 99, 53, 606/89, 86, 92, 100, 102, 105, 54; 623/22.12

(56) References Cited

U.S. PATENT DOCUMENTS

| | | | | |
|---|---|---|---|---|
| 5,122,145 A | * | 6/1992 | Fishbane | 606/102 |
| 5,603,717 A | * | 2/1997 | Benson | 606/102 |
| 5,616,147 A | * | 4/1997 | Gadelius | 606/102 |
| 5,700,268 A | * | 12/1997 | Bertin | 606/102 |
| 6,165,177 A | * | 12/2000 | Wilson et al. | 606/100 |
| 6,193,724 B1 | * | 2/2001 | Chan | 606/102 |
| 6,302,890 B1 | * | 10/2001 | Leone, Jr. | 606/91 |

\* cited by examiner

*Primary Examiner*—Pedro Philogene
(74) *Attorney, Agent, or Firm*—Malloy & Malloy, P.A.

(57) ABSTRACT

A pelvic alignment assembly and method for its use during a total hip replacement surgery in order to accurately reposition the patient's pelvis in a true anterior-posterior or true lateral position so as to optimize the accurate positioning of a prosthetic acetabular cup into the patient's hip joint socket. The assembly includes an elongated pin having one end anchored to the pelvis of the patient and a base removably inter-connected to the pin. A mounting member is movably connected to the base and is movable to adjust the relative positions of the base and mounting member in order to dispose an orientation indicator, such as a level structure, fixedly secured to the base, into a predetermined aligned or reference orientation. Prior to implanting the acetabular cup into the pelvis, the base, mounting member and level structure are repositioned on the pin and the patient is physically manipulated so as to re-orient the level structure back into the predetermined aligned or reference position thereby providing visual indication to the surgeon that the pelvis is re-oriented in the true anterior-posterior or true lateral position.

22 Claims, 6 Drawing Sheets

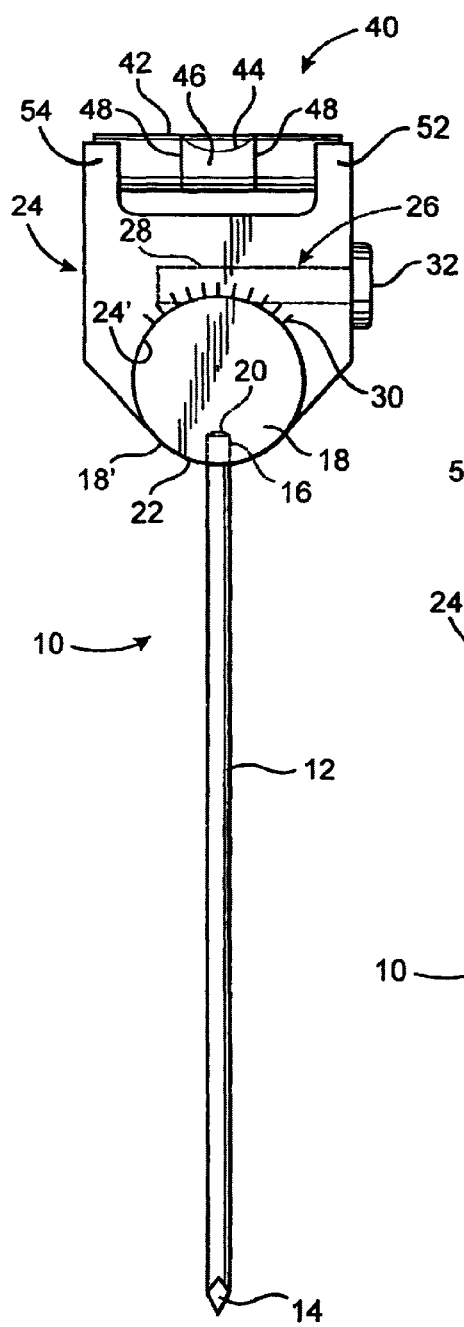
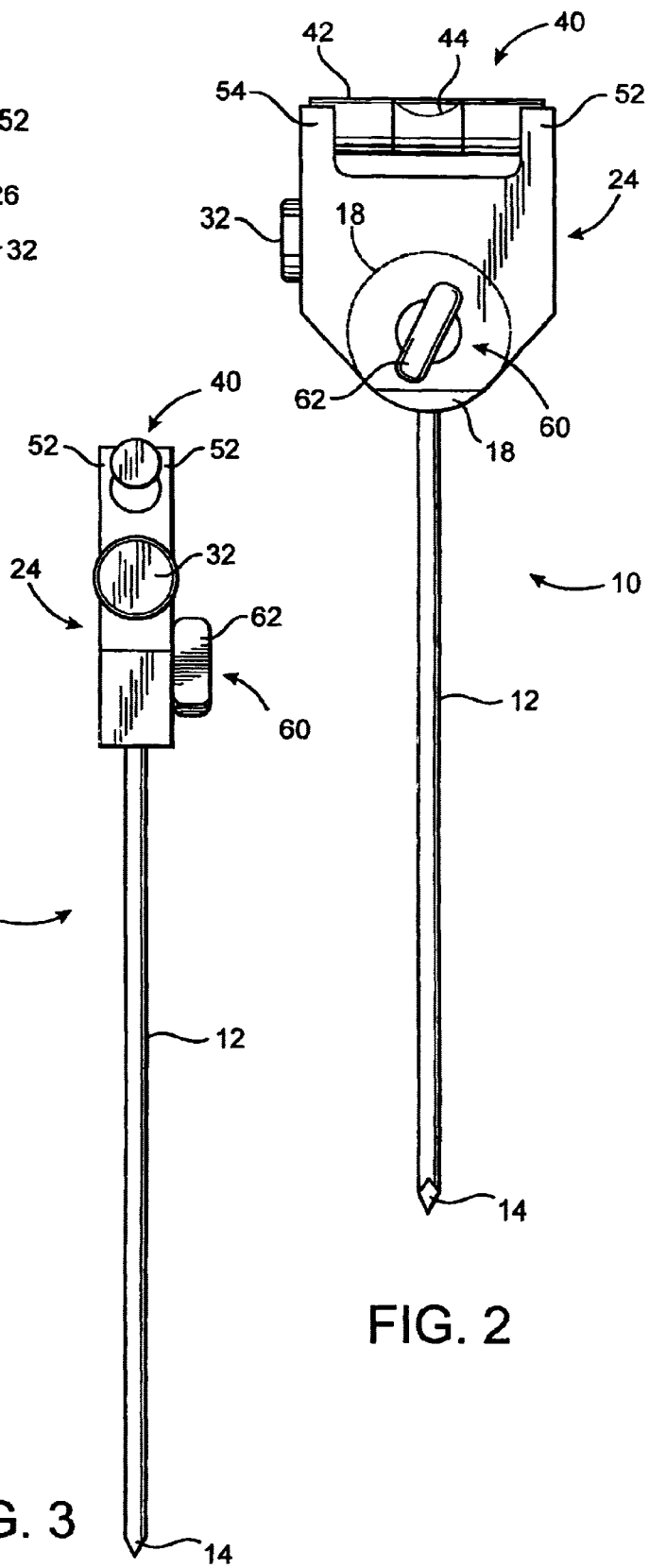
FIG. 1
FIG. 3
FIG. 2

PELVIC ALIGNMENT ASSEMBLY

CLAIM OF PRIORITY

The present application is a continuation-in-part application of previously filed, application having Ser. No. 09/526,896, filed on Mar. 16, 2000, and which is set to mature into U.S. Pat. No. 6,302,890 on Oct. 16, 2001.

BACKGROUND OF THE INVENTION

1. Field of the Invention

This invention is directed to a pelvic alignment assembly designed to be used during a total hip replacement surgery for purposes of accurately positioning a prosthetic acetabular cup in the hip joint socket by reproducing precise anatomical alignment of the pelvis. More in particular, immediately prior to the insertion of the acetabular cup, a surgeon utilizing the pelvic alignment assembly of the present invention can reposition the patient, typically by forward or backward rotation of the patient, and determine when the pelvis has accurately assumed a pre-determined "baseline" or reference position, initially established at the beginning of the surgical procedure, which is substantially indicative of a true lateral position or a true anterior-posterior position of the pelvis, and thereby, optimize the accurate positioning of the acetabular cup within patient's the hip joint socket.

2. Description of the Related Art

As people age, it is relatively common for there to be some deterioration of the hip joint, and more in particular, of the head of the femur or thigh bone, with the result often being that many such persons will have to undergo a total hip replacement ("THR") surgery performed by an orthopedic surgeon. A total hip replacement surgery involves the use of a prosthetic femoral component comprised of a stem that fits into the upper femur. On the upper or proximal aspect of the stem is a ball which will function to replace the patient's damaged or worn out of femoral head. To accommodate placement and positioning of the femoral component within the hip joint, it is necessary to insert a prosthetic acetabular cup to receive the ball-like end of the femoral component in substitution for the socket of the human hip joint. In order to achieve optimum performance of these cooperative prosthetic components, the acetabular cup must be positioned as accurately as possible within the pelvis of the patient. Inaccurate positioning or alignment of the acetabular cup within the hip joint can present extensive and serious problems to the patient after surgery and the requisite healing period, such as providing the patient with a decreased range of motion, the subsequent and possibly accelerated loosening or failure of either or both of the acetabular and femoral components, as well as possible dislocation of the hip joint. Following surgery and progressively over the first year subsequent to surgery, scar tissue normally forms about the inserted prosthetic components, which serves to recreate a hip joint capsule called a pseudocapsule which typically aids in the prevention of hip dislocation. However, when the acetabular cup is oriented in a less than an optimal angular position, hip dislocation is thought to be much more likely even when the patient is performing normal, everyday activities which require the hip joint to pass through a normal range of motion. Hip dislocation is one of the most dreaded complications after THR surgery and it is quite well understood in the medical profession that the most common reason for post-operative total hip dislocation is less than optimally positioned acetabular components, also known as acetabular malposition.

In properly orienting the acetabular cup for receipt of the prosthetic femoral component, it is necessary to accurately establish both the abduction angle as well as the anteversion angle. Typically, the anteversion angle, also known as forward flexion, is generally in the range of about 10 degrees to about 25 degrees. The abduction angle is typically in the range of about 35 degrees to 50 degrees, with a most preferred angle being at or about 45 degrees. Due to the well recognized fact that an improperly positioned acetabular component can subsequently cause the patient numerous problems, as set forth above, a number of devices or instruments have been designed to aid in the proper positioning and/or alignment of the acetabular cup.

These known devices have included cup positioners which comprise a pusher ball that is sized and shaped to fit the recess formed within the acetabular component, along with one or more positioned arms, a positioned flange juxtaposed to the pusher ball and a pusher arm connected to the ball and to the flange, to enable the user to push the acetabular cup, when it is resting on the flange into the patient's prepared acetabulum during the THR surgery. However, in the utilization of such devices, the pelvis of the patient should have been properly oriented in either a true anterior-posterior or a true lateral position in order to accomplish an optimal, predicted cup position.

There has been, unfortunately, almost a complete lack of devices in the medical field to help with accurately achieving an established pelvic position. This has left the surgeon to estimate, to the best of his or her ability, the position or alignment of the pelvis in order to utilize the known devices or instruments, of the type discussed above, for positioning of the prosthetic acetabular cup within the hip joint. Estimation of the pelvic position, in the manner set forth above, frequently involves only the surgeon's visual observation of the patient's orientation in an effort to accomplish the desired pelvic alignment. Such estimations are further encumbered by relatively little of the patient's body being exposed during surgery because of the sterile surgical drapes covering the patient. As such, it is not uncommon to misjudge the anatomical alignment of the pelvis, particularly where the patient suffers from obesity, congenital abnormalities, or bone and/or soft tissue destruction from previous surgeries.

In addition, there are close tolerances involved in accurately establishing both the anteversion angle and the abduction angle, discussed above. Therefore, the use of known devices of the type set forth above, or the unintentional failure to accurately determine the anatomical alignment of the pelvis in a true anterior-posterior or true lateral position, may very well result in the acetabular component being improperly positioned when implanted into the pelvis of the patient.

Accordingly, there is a long felt need in the medical field for reliable, medical instrumentation which would be capable of accurately establishing a proper or preferred anatomical position of a patient's pelvis, which may be defined to mean a true anterior-posterior position or a true lateral position of the pelvis during a THR surgery. More in particular, prior to the implantation of the acetabular cup into the patient's pelvis, the pelvis should be repositioned into a predetermined position in order to optimally implant and orient the acetabular component related to the prosthetic femoral component. As discussed above, implementation of the acetabular cup is optimally accomplished if the pelvis of the patient is properly oriented in either a true anterior-posterior or a true lateral position. If an alignment assembly were developed to properly re-orient the patient in such a position, it would greatly enhance the surgeon's ability to optimally and reproducibly position the acetabular cup. The patient would be more likely to function through a normal range of movement, with a greatly decreased fear of either hip dislocation or accelerated deterioration of the implanted prosthetic components. If any such alignment assembly were developed, it would preferably include a visually observable instrument structured to facilitate the establishment and/or re-establishment of a baseline or reference position of the pelvis, when in its normal or proper anatomical alignment defined by a true anterior-posterior position or true lateral position. More specifically, any such alignment assembly should be structured so as to be capable of being adjustably oriented or positioned to reestablish the aforementioned baseline or reference position, indicative of proper pelvic alignment of the patient, and thereby, to more reliably assure the accurate placement of the acetabular cup.

SUMMARY OF THE INVENTION

The present invention is designed to address these and other needs which remain in the art and comprises an alignment assembly, The alignment assembly of the present invention is designed to assist with the accurate positioning of a prosthetic acetabular cup into the pelvis of a patient during a total hip replacement (THR) surgery. More specifically, the alignment assembly of the present invention allows the surgeon to accurately orient the pelvis by repositioning it into a previously established or baseline position of proper anatomical alignment, wherein the patient is positioned in a true anterior-posterior or a true lateral position, depending on the surgical approach which the surgeon elects to use.

In at least one preferred embodiment the alignment assembly of the present invention comprises an elongated pin such as, but not limited to, a Steinmann pin. The distal end of the elongated pin is specifically structured to be anchored into the pelvis so as to extend outwardly therefrom. The alignment assembly further comprises a base removably mounted on the opposite, outwardly extending, proximal end of the elongated pin, with the base being movably connected to a mounting member. The mounting member includes a socket dimensioned and configured to removably receive the outwardly extending, proximal end of the elongated pin therein, so as to allow stable but removable support and attachment of the base to the elongated pin.

The alignment assembly additionally comprises an adjustment assembly, which is mounted at least in part on the base and which is at least partially interconnected to the mounting member. The adjustment assembly is specifically designed to be accessed from the exterior of the base by being manipulated by the surgeon or other medical personnel. Selective adjustment of the relative positions between the base and the mounting member is thereby accomplished, as will be explained in greater detail hereinafter.

The alignment assembly additionally includes a visually observable instrument or orientation indicator structured to facilitate the establishment and/or re-establishment of a baseline or reference position of the patient's pelvis in a normal or proper anatomical alignment defined by a true anterior-posterior position or true lateral position. The visually observable instrument or orientation indicator preferably, but not necessarily, comprises a level structure in the form of a "bubble-type" of level secured to the base and moveable therewith. Further, the level structure is disposed on the base in a position which is readily observable by the surgeon and/or other medical personnel, while the base is supported on the proximal end of the pin, due to the interconnecting disposition of the mounting member, as generally set forth above.

It is emphasized that while the preferred embodiment comprises the orientation indicator in the form of a bubble type level, a variety of other indicators could be utilized. Such additional orientation indicators would preferably be visually observable and include electrical, digital and/or mechanical structures which sense and clearly indicate a proper orientation of the base. The aforementioned baseline or reference position indicative of the patient's pelvis being disposed in a normal or proper anatomical alignment would thereby be established.

In addition, the base of the alignment assembly particularly when using a level structure, preferably includes a locking assembly that is operatively connected to the mounting member as well as the base in a manner which is capable of being selectively positioned in either a locked or an unlocked position. The locked position prevents or significantly restricts movement between the base and the mounting member, thereby preventing operation of the adjustment assembly for purposes of changing the position of the base relative to the mounting member. With the locking assembly disposed in the locked position, the surgeon is reasonably assured that the intended position of the level structure relative to the elongated pin may be re-established, when necessary to accomplish the predetermined established anatomical alignment of the pelvis, immediately prior to insertion of the acetabular cup. Further, proper use and observation of the level structure or other orientation indicator allows the surgeon to reestablish the required pelvic alignment through minimal physical manipulation or repositioning of the patient, immediately prior to the insertion of the acetabular cup into the pelvis.

In one preferred embodiment, use of the alignment assembly of the present invention during a THR surgery involves positioning the patient into a true anterior-posterior or true lateral position on the operating table. After appropriate preparation and draping of the patient, the distal end of the elongated Steinmann pin is anchored to the iliac crest of the patient's pelvis. Initial alignment of the pelvis is accomplished by orienting the elongated pin in an approximately perpendicular relation to the floor, ground or other supporting surface. The base, being movably connected to the mounting member, is supported on the pin by attaching the mounting member to the outwardly extending or proximal end of the pin. While the base remains supported on the pin, the adjustment assembly is manipulated by the surgeon or other medical personnel until the level structure, fixedly secured to the base and movable therewith, indicates that it is oriented into a true horizontal or other applicable reference position. The locking assembly is then manipulated into the locked position, thereby assuring a relative fixed orientation of the level structure relative to the pin, when the base is mounted thereon. The base, along with the mounting member and the level structure, can then be removed from the outwardly extending end of the pin, while the distal end of the pin remains anchored into the pelvis. The surgical procedure associated with a total hip replacement or THR then proceeds to the point where the acetabular cup is ready for insertion into the hip joint socket of the pelvis. Immediately prior to the insertion of the acetabular cup, the base is again supported on the elongated pin by reattaching the mounting member to the proximal end. The locking assembly still maintains the level in its previously, predetermined fixed position relative to the pin. Accordingly, in order to re-orient or position the level structure into the true horizontal or established reference orientation, which was established by locking the mounting member to the base, the patient is then physically moved, such as by rotating the patient, preferably forward or backward, to once again orient the level structure in the predetermined, initially established baseline or reference position. Visual observation of the level structure indicates to the surgeon or other medical personnel, such as when the preferred "bubble" is appropriately located or "centered" within the level structure, that the level structure, the elongated pin and accordingly, the pelvis is re-oriented in the same, pre-determined established anatomical alignment for optimizing the accurate positioning and insertion of acetabular cup.

The objects and features of the present invention set forth above are intended to be illustrative only and should not be construed as limiting in any way. In fact, these and other objects, features and advantages associated with the present invention should become more evident from the drawings and the detailed description of the preferred embodiments for the invention, which follow.

BRIEF DESCRIPTION OF THE DRAWINGS

For a fuller understanding of the nature of the present invention, reference should be had to the following detailed description taken in connection with the accompanying drawings in which:

FIG. 1 is a front view of the alignment assembly of the present invention.

FIG. 2 is a side view of the alignment assembly illustrated in FIG. 1.

FIG. 3 is a rear view of the alignment assembly illustrated in FIGS. 1 and 2.

Like reference numerals refer to like parts throughout the several views of the drawings.

DETAILED DESCRIPTION OF THE PREFERRED EMBODIMENT

Figure 4:
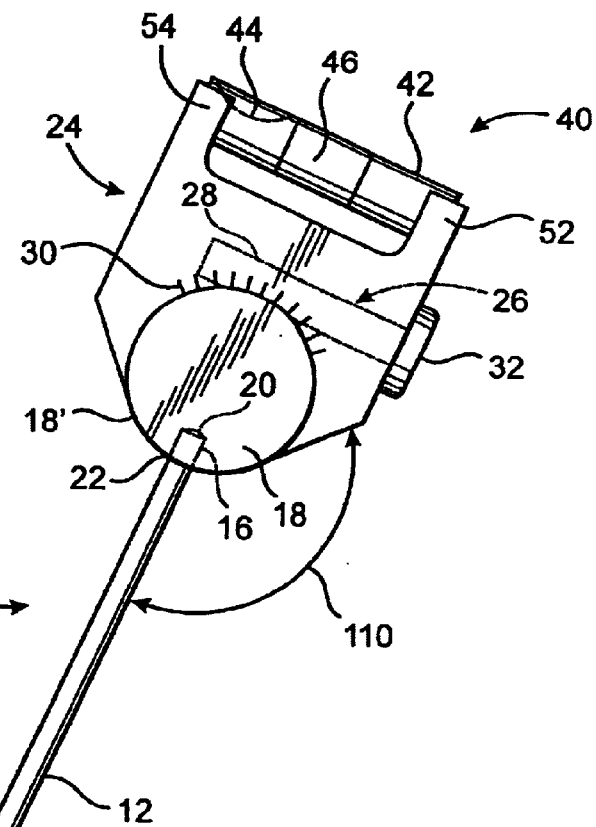
FIG. 4 is a front view of the alignment assembly of the present invention as initially inserted in predetermined relation to the pelvis of a patient involved in a total hip replacement (THR) surgery.
Figure 4:
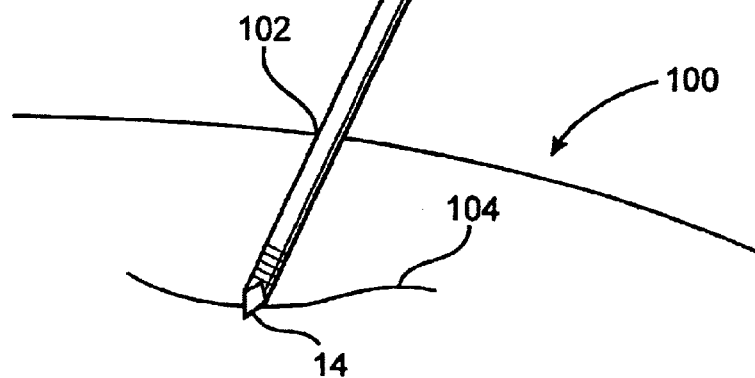

As shown in the accompanying Figures, the present invention is directed to an alignment assembly designed generally for use in a total hip replacement (THR) surgery, and more specifically, is structured to optimize the positioning and orientation of a prosthetic acetabular cup into the pelvis of a patient during THR surgery. More specifically, the alignment assembly allows a surgeon or other medical personnel to establish a baseline or reference position of the patient, when the pelvis is disposed in an accurate, anatomically aligned position, thereby facilitating accurate placement of the acetabular component into the pelvis during the THR. As will be explained in greater detail hereinafter, the pelvic alignment assembly of the present invention allows the surgeon or other medical personnel to orient the patient's pelvis in order to establish a predetermined, baseline or reference position at the beginning of a THR surgery, and to subsequently determine that baseline reference orientation and re-establish it by physical manipulation of the patient immediately prior to the insertion of the acetabular cup into the patient's pelvis.

With reference to FIGS. 1 through 5, one preferred embodiment of the alignment assembly of the present invention is shown in assembled formed and is generally indicated by reference numeral 10. The alignment assembly 10 includes an elongated pin 12, which may comprise a type of pin well known in the medical field as a Steinmann pin. The elongated pin 12 has a distal end 14 which is preferably threaded, sharpened, or otherwise structured to facilitate its being anchored into the pelvis of a patient during a THR surgical procedure. The opposite or proximal end 16 of the elongated pin 12 is rounded, blunted or otherwise structured for removable support and attachment to a mounting member 18. Attachment of the mounting member 18 to the proximal end 16 of pin 12 is preferably accomplished through the provision of a socket or like structure 20, having an open end 22, wherein the socket 20 and the open end 22 are both disposed and dimensioned to receive the proximal end 16 of pin 12 on the interior of the mounting member 18 in a manner which facilitates the stable but removable support of the mounting member 18 thereon.

The alignment assembly of the present invention also comprises a housing or base, generally indicated as 24, which is movably connected to the mounting member 18, such that the relative positions between the base 24 and the mounting member 18 can be selectively varied, for reasons to be explained in greater detail hereinafter. As best shown in FIG. 1, the mounting member 18 preferably has a curved and/or at least partially circular configuration, such that a portion of the periphery 18' of the mounting member 18 is at least partially enclosed or otherwise disposed in immediately adjacent relation to an interior recess 24' or like receiving portion of the base 24. The recess 24' is cooperatively configured and structured A with the mounting member 18 so as to facilitate a stable but adjustably movable connection between the base 24 and the mounting member. Due to the fact that the mounting member 18 and the base 24 are relatively movable, the open end 22 of the receiving socket 20 is disposed on an exposed portion of the periphery 18' of mounting member 18. Accordingly, regardless of the relative orientations of the mounting member 18 or the base 24, the open end 22 of socket 20 will nearly always be exposed, so as to allow insertion or removal of the proximal end 16 of the elongated pin 12.

The alignment assembly of the present invention also comprises an adjustment assembly, generally indicated as 26. The adjustment assembly 26 is mounted, at least in part, on the base 24 and is structured to accurately adjust the positioning of the base 24 relative to the mounting member 18. The adjustment assembly 26 may include a drive gear represented in phantom lines in the various Figures and indicated as 28. In addition, the adjustment assembly 26 includes a driven gear 30 formed at least in part on the mounting member 18 and disposed in mating engagement with the drive gear 28. The driven gear 30 may be more accurately represented as a gear segment extending along the periphery 18' or other portion of the mounting member 18, generally on the interior of the base 24, so as to be accurately disposed in mating engagement with the elongated drive gear 28. It should be emphasized that the aforementioned gear assembly, including drive gear 28 and driven gear or gear segment 30, could take a variety of different structural configurations, other than that shown in order to accomplish the selective and accurate orientation of the base 24 relative to the mounting member 18.

The adjustment assembly 26 also includes a control portion 32, preferably in the form of a knob being exteriorly accessible on the base 24 and connected to the drive gear 28 so as to rotate therewith. The disposition and dimension of the control knob 32 is such as to be easily manipulated by the surgeon or other medical personnel during the surgical procedure in a manner which will not distract the surgeon or interfere with the surgical procedure. As will be explained in greater detail with reference to FIGS. 4 and 5, manipulation of the control knob 32 will allow the surgeon or other medical personnel to position the base 24 relative to the mounting member 18 and into a preferred orientation.

Figure 5:
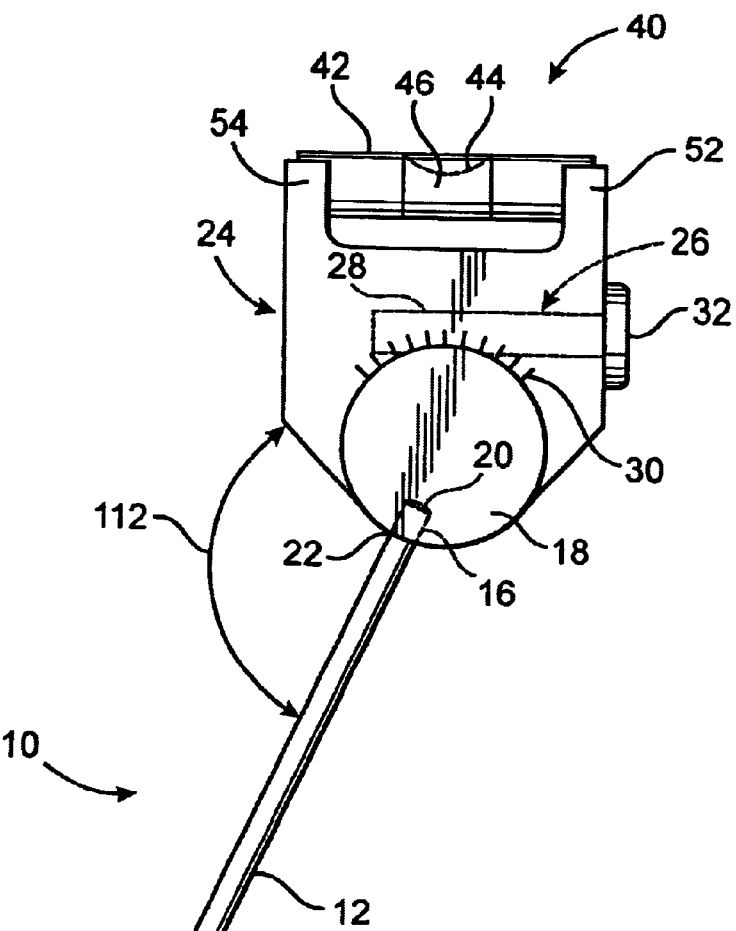
FIG. 5 is a front view of the alignment assembly of the present invention with the housing positioned and locked into a horizontal orientation indicated by a bubble of the associated level being disposed in a centered position, and thereby defining a reference or baseline position of an anatomically aligned pelvis.
Figure 5:
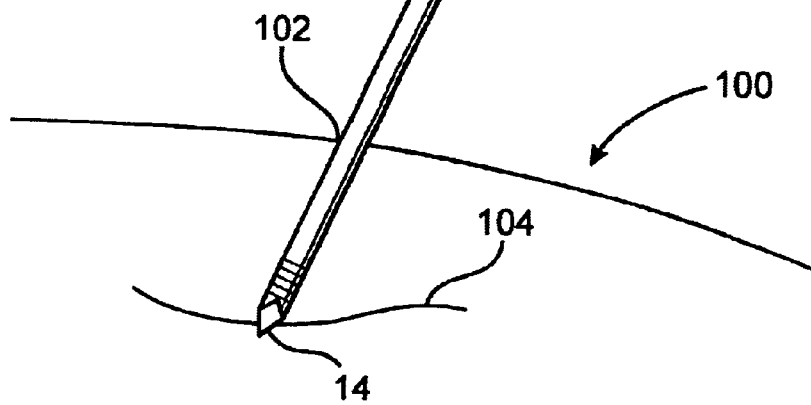

The alignment assembly 10 of the present invention also comprises a visually observable orientation indicating instrument such as, but not limited to, a level structure, generally indicated as 40 throughout the various Figures. In the embodiments shown, the level structure 40 comprises a "bubble" level having a sealed outer casing 42, partially filled with a liquid and specifically structured to include an air or gas bubble 44, which freely travels along the interior of the casing 42 dependent on the orientation of the casing 42. With reference to FIGS. 1, 3 and 5, the bubble is shown in a center position 46, as can be readily determined by the existence of spaced apart markings 48 formed on the sealed casing 42 and correspondingly disposed and dimensioned relative to one another to accurately align with the length and/or position of the bubble 44, when the casing 42 is in a true horizontal position. As shown in FIG. 4, orientation of the casing 42 of level 40 in an angular position, other than true horizontal, serves to automatically position the bubble 44 out of alignment with the center position 46, such as at one end of casing 42.

The level structure 40 is preferably fixedly secured to the base 24 so as to be movable therewith. For example, the upper end of the base 24 may include a cradle-like structure defined by two pairs of spaced apart arms 52, 52 (see FIGS. 2 and 3) and 54, 54, each pair disposed at respective ends of the cradle-like structure. As such, the level structure 40 is disposed in a position which is clearly and easily observable by the surgeon or other medical personnel during the THR surgery. Accordingly, movement of the base 24 relative to the mounting member 18, preferably through manipulation of the control knob or portion 32 of the adjustment assembly 26, will cause repositioning or orientation of the level structure 40, due to the fact that it is secured to the base 24 so as to move therewith, as set forth above.

Another structural feature of the present invention is the incorporation of a locking assembly, generally indicated as 60 and best shown in FIGS. 2 and 3. The locking assembly 60 preferably includes a wing nut or like member 62, exteriorly protruding from a rear surface or other portion of the base 24. The wing nut or like member 62 may be interconnected to the mounting member 18 as well as to a portion of the base 24. Therefore, a "tightening" of the member 62 will accomplish a removable, locking engagement between the base 24 and the mounting member 18, so as to prevent relative movement therebetween, even during inadvertent attempts to rotate or otherwise manipulate the control knob 32. Therefore, the position of the base 24 and accordingly, of the level structure 40 relative to the mounting member 18 can be secured in order to establish a reference or baseline position of the mounting member 18, base 24 and level structure 40, relative to the elongated pin 12, which has been placed in the pelvis of the patient, as will be explained in greater detail hereinafter, primarily with reference to FIGS. 4 and 5.

Figure 8:
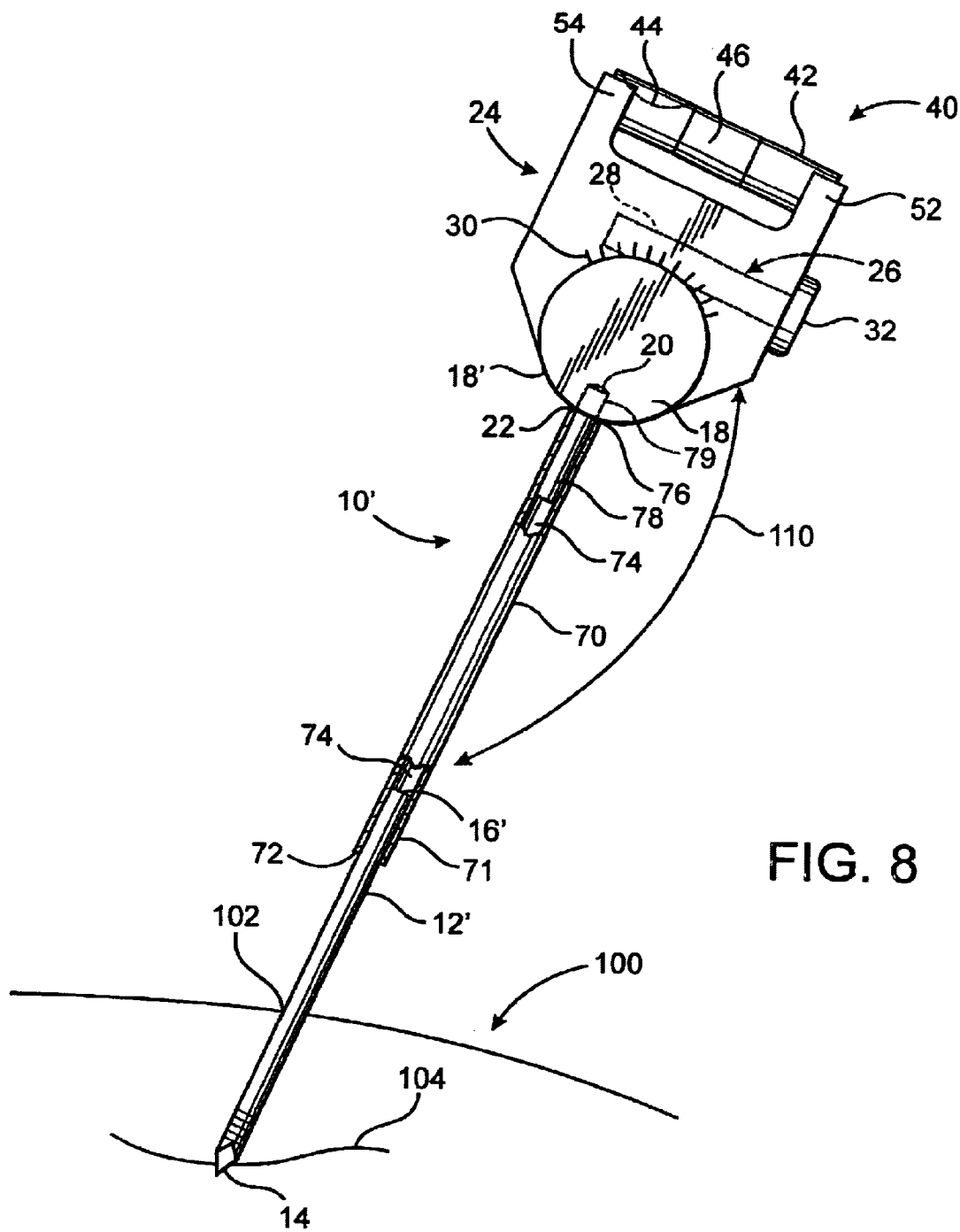
FIG. 8 is a front view of the alignment assembly of the embodiment of FIG. 6 in an initially applied orientation.
Figure 9:
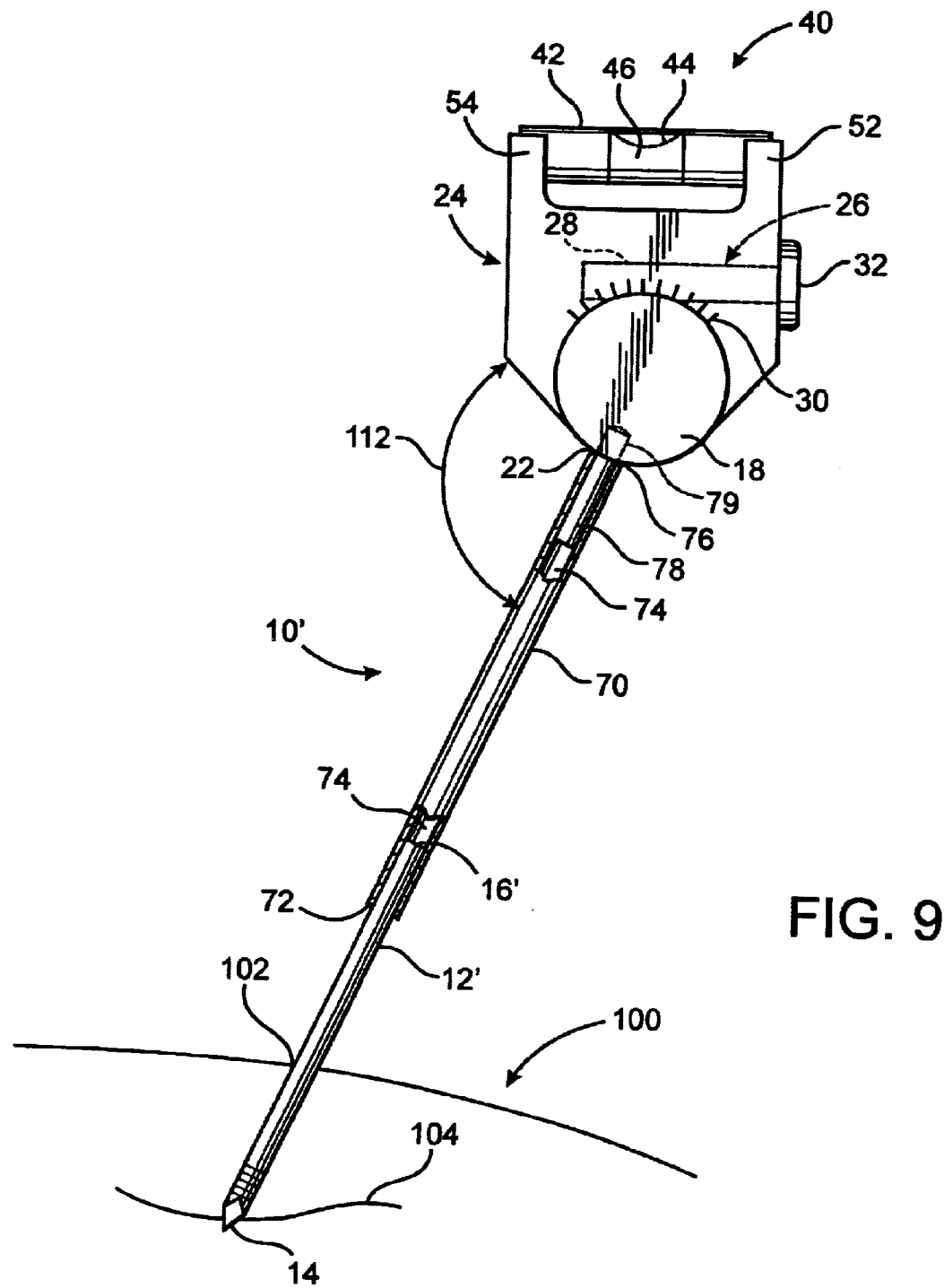
FIG. 9 is a front view in partial cutaway of the alignment assembly of the embodiment of FIG. 6 oriented in a predetermined aligned or reference position.

Utilizing the alignment assembly 10 of the present invention, positioning of a prosthetic acetabular cup during a total hip replacement (THR) surgery is optimally positioned by accurately accomplishing proper anatomical alignment defined by a true anterior-posterior or true lateral position of the pelvis. Once the patient is properly oriented, as set forth above, the pelvic alignment assembly 10 is applied as best demonstrated in FIGS. 4 and 5. More specifically, the patient, generally indicated as 100, is appropriately prepared and draped as part of the normal surgical procedure. Subsequently, the elongated pin 12 which, as set forth above may be a Steinmann pin, is inserted into the patient 100 hip area, preferably at the site of a small incision 102. Upon insertion, the distal end 14 of the pin 12 is anchored into the pelvis of the patient, and more preferably, into the iliac crest schematically represented as 104. The pin 12 is preferably anchored in an orientation which is approximately perpendicular to the ground or other supporting surface or reference object. For purposes of emphasizing the structural features and operational effectiveness of the alignment assembly 10, the pin 12 is represented in FIGS. 8 and 9 as being more angularly oriented rather than being substantially perpendicular, as set forth above. Once the pin 12 is appropriately anchored into the iliac crest 104, the base 24 is removably secured to the proximal end 16 of the pin 12, by inserting the proximal end 16 through the exposed open end 22 and receiving socket 20 of the mounting member 18, as shown in FIG. 4.

Upon initially mounting the base 24 on the proximal end 16 of the pin 12, the level structure 40 will most probably be oriented at an arbitrary angle, schematically indicated as 110. As shown in FIG. 5, the adjustment assembly 26 is then operated, through manipulation of the control knob 32, so as to dispose the level structure 40 into a predetermined alignment which is preferably defined by a horizontal orientation of the level structure. As set forth above, a horizontal orientation of the level 40 is capable of being easily determined by a visual indication that the bubble 44 is disposed within the center position 46, such as is shown in FIG. 5. The locking assembly 60 is then tightened through manipulation of the wing nut or other member 62, so as to prevent relative movement between the base 24 and level structure 40, and the mounting member 18 and pin 12, respectively. In this locked position, the base 24 and the level structure 40 will now be disposed at an angle 112 relative to pin 12 which differs from angle 110.

Once the locking assembly 60 has been tightened in the manner as set forth above, the base 24 can be removed from the proximal end 16 of pin 12, while the elongated pin 12 remains anchored in the pelvis 104 during the remainder of the surgical procedure or until the acetabular cup is implanted. Once the surgical procedure has proceeded to the point where the patient is ready for the insertion of the prosthetic acetabular cup, the base 24, still remaining in its locked position relative to the mounting member 18, is again mounted on the proximal end 16 of the elongated pin 12, by inserting the proximal end 16 through the open end 22 and into the interior of the receiving socket 20. The patient is then physically manipulated, normally by rotating the patient forward and backward, to once again orient the pin 12 and the level 40 into a position demonstrated in FIG. 5, wherein the bubble 44 is disposed into alignment with the center position 46. Once such alignment occurs, the surgeon is assured that the pelvis has been re-established in the proper, true anterior-posterior or true lateral position. The acetabular cup can then be inserted into the pelvis, with the pelvis being again disposed in the original reference or baseline position, initially established by originally orienting the level structure 40, at the beginning of the surgical procedure, as outlined above.

The present invention comprises additional preferred embodiments disclosed in FIGS. 6 through 9. As represented therein, an elongated pin 12' is utilized instead of the pin 12 of the embodiment of FIGS. 1 through 5. As will be noticed the elongated pin 12 has a predetermined reduced and/or restricted size in terms of a much lesser length than the elongated pin 12. The predetermined restricted size pin 12' has a distal end 14 structured to be anchored into the iliac crest 104 schematically represented in FIGS. 8 and 9. The proximal end 16' protrudes outwardly from the patient 100 a much lesser distance as a result of its reduced length than the elongated Steinman pin 12. Accordingly, the reduced size of the elongated pin 12' prevents or significantly reduces the possibility of the pin 12' being inadvertently contacted or engaged by medical personnel during the medical procedure. Inadvertent contact with the pin 12' could cause a dislodgement of the distal end 14 from the pelvis of the patient 100 and/or cause a potentially undesirable repositioning of the pin 12'. Accordingly, the reduced size or length of the pin 12' disposes the proximal end 16' outwardly from the patient 100 a much shorter distance. This in turn reduces the possibility of its inadvertent displacement.

Figure 6:
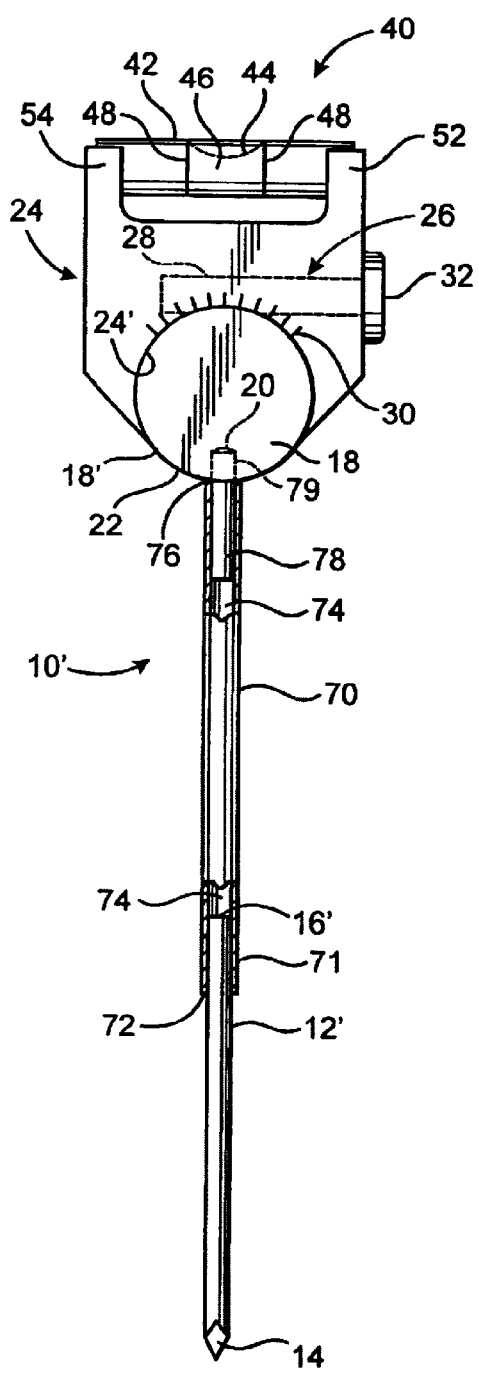
FIG. 6 is a front view in partial cutaway of another preferred embodiment of the alignment assembly of the present invention.

In order to overcome any disadvantages associated with the reduced length of the elongated pin 12', the alignment assembly 10' comprises an adaptor structure 70 having an elongated, linear configuration. Further, the adaptor structure 70 preferably comprises a tubular or sleeve like construction having a first end 71 including an open extremity 72 disposed in communicating relation with an at least partially hollow interior 74. In the embodiment of FIGS. 6, 8, and 9 the adaptor structure 70 includes an oppositely disposed second end 76 wherein the extremity thereof is open for communication with the hollow interior as at 74. The adaptor structure 70 is formed from a rigid material applicable for use in various surgical procedures and may be either disposable or be formed from a material which is capable of being sterilized using 12 conventional medical procedures.

As set forth above, it is important that an orientation 14 indicator preferably in the form of the level 40 be disposed in a location which facilitates visual observation by the surgeon or other medical personnel. Accordingly, the length of the adaptor member 70 should be sufficient to position the base 24, with the level structure 40 secured thereto, a sufficient distance outwardly from the patient 100 to accomplish such preferred visual observation. Therefore, the adaptor structure 70 is of sufficient length to extend along at least a majority of the distance between the elongated pin 12' and/or the proximal end 16' thereof and the base 24.

Connection to the base 24 in the preferred embodiment of FIGS. 6, 8 and 9 is accomplished by the provision of a connecting pin or other applicable structure 78 fixedly or removably secured to the base 24 by virtue of it being interconnected as at 69 to the mounting member 18. When it is desired to secure the base 24 in its operative position as described above and as more fully detailed hereinafter, the connecting pin 78 is telescopically disposed within the interior 74 of the adaptor structure 70 through the open extremity 76. Similarly, the opposite or first end of the adaptor structure 70 is telescopically disposed over the proximal end 16' which is extended through the open extremity 72 into the interior 74.

Removable but secure mounting of the adaptor structure 70 to both the elongated pin 12' and the connecting pin 78 can be accomplished by sufficiently close tolerances to achieve a frictional engagement therebetween. Alternatively, one or more stop members (not shown) may be mounted on or within the adaptor structure 70 and/or secured to the elongated pin 12' and/or the connecting pin 78. Accordingly, the structural features of the embodiments of FIGS. 6, 8 and 9 allow the removable mounting of the adaptor structure 70 both to the elongated pin 12' and the connecting pin 78. Also, as set forth above the connecting pin 78 may be fixedly or removably secured within the socket 20 of the mounting member 18, such as by being disposed through the open end 22 thereof.

Figure 7:
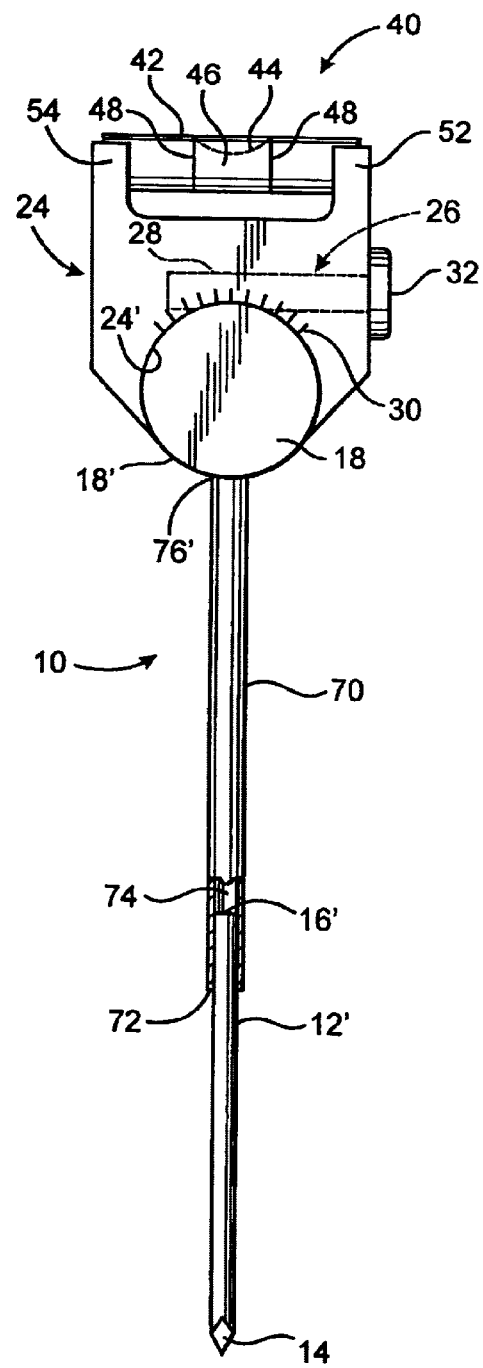
FIG. 7 is a front view of partial cutaway of yet another preferred embodiment of the alignment assembly of the present invention.

Yet another preferred embodiment of the present invention is disclosed in FIG. 7. More specifically, the adaptor structure 70 has the same or equivalent structural features as the adaptor structure 70 of the embodiment of FIGS. 6, 8 and 9. However, the second end 76' is interconnected to the base 24 by being fixedly secured to the mounting member 18 so as to move therewith. Accordingly, while the adaptor structure 70 in the embodiment of FIG. 7 is removably secured to the elongated pin 12' it is fixedly interconnected to the base 24 but movable relative thereto due to the fixed attachment between the second end 76' and the mounting member 18.

Other than the structural modifications set forth above, the preferred embodiments of FIGS. 6 through 9 are operative substantially in the same manner as the preferred embodiment of FIGS. 1 through 5. More specifically, utilizing the alignment assembly 10', optimal positioning of the prosthetic acetabular cup during a THR surgery is performed by accurately accomplishing proper an anatomical alignment of the patient, defined by a true anterior/posterior or true lateral position of the pelvis. Once the patient is properly oriented as set forth above, the pelvic alignment assembly 10' is applied as best demonstrated in FIGS. 8 and 9. More specifically the patient, generally indicated as 10 is appropriately prepared and draped as part of the normal surgical procedure. Subsequently, the elongated pin 12' having a predetermined reduced or restricted longitudinal dimension, is inserted into the hip area of the patient 100 preferably through the small incision 102.

Upon insertion, the distal end 14 of the pin 12' is anchored into the iliac crest 104 of the patient 100, as schematically represented. While the pin 12' is preferably anchored in a substantially perpendicular orientation relative to the ground or other supporting surface, the angular orientation represented in FIGS. 8 and 9 is provided for purposes of clarity in further emphasizing both the structural and operative features of the alignment assembly 10'. Accordingly, once the pin 12' is appropriately anchored into the crest 104, the adaptor structure 70 is mounted on the proximal end 16' of the elongated pin 12'. When utilizing the embodiment of FIGS. 6, 8 and 9, the opposite or second end 76, is telescopically disposed about the connecting pin 78 to it accomplish a stable yet removable attachment thereto. The base 24, while adjustably movable relative to the adaptor 70 and pin 12', is also removably interconnected to the pin 12'.

Upon initially interconnecting the base 24 to the elongated pin 12', the orientation indicator, preferably in the form of the level structure 40, will most probably be oriented at an arbitrary angle, schematically oriented as 110 in FIG. 8. The adjustment assembly 26 is then operated so as to dispose the level structure 40 into a predetermined alignment which is preferably defined by a horizontal orientation of the level structure. It should be noted that when an orientation indicator other than a level structure is utilized, the orientation thereof into a predetermined aligned position can be accomplished in a similar manner.

Assuming the utilization of level structure 40, a horizontal orientation thereof is easily determined by the visual indication of the bubble 44 being disposed within the center position 46. Locking assembly 60 is then tightened through manipulation of the knob or like member 72 so as to prevent relative movement between the base 24 and the level structure 40 and the mounting member 18 and elongated pin 12', respectively. In this locked position, the base 24 and the level structure 40 will now be disposed at an angle 112 shown in FIG. 9 relative to the pin 12' which differs from the angle 110 of FIG. 8.

Once the locking assembly 70 has been tightened in the manner set forth above, the base 24 can be removed from the adaptor structure 70 when utilizing the embodiment of FIGS. 6, 8, and 9. When utilizing the embodiment of FIG. 7, the base is removed from the pin 12' by disconnecting the proximal end 16' from the interior 74 of the adaptor 70 as should be evident.

Regardless of which of the preferred embodiments of FIGS. 6 through 9 are utilized, once the surgical procedure has proceeded to the point where the patient is ready for the insertion of the prosthetic acetabular cup, the base 24 is again mounted or interconnected to the pin 12' by reconnecting the adaptor structure 70 to both the connecting pin 78 and the elongated pin 12', in the manner set forth above. Such reconnection of the base 24 to the pin 12' utilizing the embodiment of FIG. 7 is accomplished by inserting the proximal end 16' through the open extremity 72, wherein the opposite or second end 76' is fixedly attached thereto.

The patient is then physically manipulated, normally by rotating the patient forward and/or backward, to once again orient the pin 12' and the orientation indicator in the form of the level 40 into a position demonstrated in FIG. 9. In such a position, the bubble 44 is disposed into alignment with the center position 46. Once such alignment occurs, the surgeon is assured that the pelvis has been re-established in the proper, true interior-posterior or true lateral position. The acetabular cup can then be inserted into the pelvis, with the pelvis being again aligned in the original reference or baseline position, initially established by properly orienting the level structure 40, at the beginning of the surgical procedure, as it outlined above.

Since many modifications, variations and changes in detail can be made to the described preferred embodiment of the invention, it is intended that all matters in the foregoing description and shown in the accompanying drawings be interpreted as illustrative and not in a limiting sense. As one example only, other level structures aside from a bubble level could be utilized with the present invention, such as a laser level. Thus, the scope of the invention should be determined by the appended claims and their legal equivalents.

Now that the invention has been described,

What is claimed is:

1. An alignment assembly designed to aid with the accurate re-orientation of the pelvis of a patient during a surgical procedure, said alignment assembly comprising:

a) an elongated pin structured to be anchored to the patient's pelvis,
   b) a base including an orientation indicator secured thereto and disposed to facilitate visual observation thereof,
   c) an adaptor removably interconnecting said pin and said base, and
   d) said orientation indicator adjustable relative to said pin into a predetermined aligned position indicative of a true anterior-posterior position or true lateral position of the pelvis.

2. An alignment assembly as recited in claim 1 wherein said adaptor is removably connected to said pin.

3. An alignment assembly as recited in claim 2 wherein said adaptor is removably connected to said base.

4. An alignment assembly as recited in claim 2 wherein said adaptor is fixedly interconnected to said base.

5. An alignment assembly as recited in claim 2 wherein said adaptor comprises an elongated configuration including a first end removably connected to said pin and a second end fixedly interconnected to said base.

6. An alignment assembly as recited in claim 5 wherein said first end of said adaptor is structured to be telescopically connected to said pin.

7. An alignment assembly as recited in claim 6 wherein at least said first end comprises a tubular configuration including an open extremity, said first end dimensioned to at least partially enclose an exposed proximal end of said pin.

8. An alignment assembly as recited in claim 7 wherein said pin and said adaptor both comprise a linear configuration interconnected in coaxial alignment with one another.

9. An alignment assembly as recited in claim 2 wherein said pin comprising a linear configuration of a predetermined restricted length.

10. An alignment assembly as recited in claim 9 wherein said pin includes a distal end structured to be anchored the patient's pelvis and a proximal end extending outwardly from the patient.

11. An alignment assembly as recited in claim 10 wherein said adaptor comprising an elongated linear configuration including a first end removably connected to said proximal end of said pin.

12. An alignment assembly as recited in claim 11 wherein said first end of said adaptor is structured to be telescopically connected to said pin and comprises a tubular configuration including an open extremity and a hollow interior communicating with said open extremity.

13. An alignment assembly as recited in claim 10 wherein said adaptor comprises an elongated linear configuration including a first end removably connected to said proximal end of said pin and a second end interconnected to said base; said adaptor including a length sufficient to extend from said proximal end along at least a majority of the distance between said pin and said base.

14. An alignment assembly as recited in claim 13 wherein said pin and said adaptor comprise a collective length sufficient to dispose said orientation indicator outwardly from the patient a sufficient distance to facilitate visual observation thereof.

15. An alignment assembly as recited in claim 14 further comprising a mounting member disposed in interconnecting relation between said adaptor and said base; said base and said orientation indicator movably adjustable relative to said mounting member and said adaptor, said adaptor being connected to said pin so as to move therewith relative to said base.

16. An alignment assembly as recited in claim 15 wherein said orientation indicator comprises a level structure.

17. A alignment assembly designed to aid with the accurate reorientation of the pelvis of a patient during a surgical procedure, said alignment assembly comprising:
   a) an elongated pin of a predetermined restricted length,
   b) a base including an orientation indicator secured thereto and movable therewith,
   c) a mounting member adjustably connected to said base,
   d) an adaptor connected to said mounting member and removably interconnecting said pin to said base, and
   e) said base selectively movable relative to said pin and said adaptor for disposition of said orientation indicator into a predetermined aligned position indicative of a true interior-posterior position or true lateral position.

18. An alignment assembly as recited in claim 17 wherein said pin includes a linear configuration having a distal end structured to be anchored to a patient's pelvis and a proximal end extending outwardly from the patient.

19. An alignment assembly as recited in claim 18 wherein said adaptor comprises an elongated linear configuration including a first end removably connected to said proximal end of said pin and a second end interconnected to said mounting member; said adaptor including a length sufficient to extend from said proximal end along at least the majority of the distance between said pin and said base.

20. An alignment assembly as recited in claim 19 wherein said first end of said adaptor comprises a hollow interior and an open extremity communicating therewith; said first end telescopically mounted on said proximal end.

21. An alignment assembly as recited in claim 17 further comprising an adjustment assembly structured to selectively vary the position of said base relative to said pin so as to dispose said orientation indicator into said predetermined aligned position.

22. An alignment assembly as recited in claim 21 wherein said orientation indicator comprises a level structure secured to said base and movable therewith, said level structure disposed into a horizontal orientation which defines said predetermined aligned position.

* * * * *